US010894138B2

(12) United States Patent
Bateman et al.

(10) Patent No.: US 10,894,138 B2
(45) Date of Patent: Jan. 19, 2021

(54) TRACHEOSTOMY TUBE ASSEMBLIES AND INNER CANNULAE

(71) Applicant: SMITHS MEDICAL INTERNATIONAL LIMITED, Ashford (GB)

(72) Inventors: Timothy Bateman, Hythe (GB); Stephen James Field, Canterbury (GB); Andrew Thomas Jeffrey, Hythe (GB); Christopher John Woosnman, Great Sutton (GB)

(73) Assignee: Smiths Medical International Limited, Ashford (GB)

( * ) Notice: Subject to any disclaimer, the term of this patent is extended or adjusted under 35 U.S.C. 154(b) by 356 days.

(21) Appl. No.: 15/574,271

(22) PCT Filed: May 27, 2016

(86) PCT No.: PCT/GB2016/000108
§ 371 (c)(1),
(2) Date: Nov. 15, 2017

(87) PCT Pub. No.: WO2016/198818
PCT Pub. Date: Dec. 15, 2016

(65) Prior Publication Data
US 2018/0133425 A1 May 17, 2018

(30) Foreign Application Priority Data
Jun. 11, 2015 (GB) .................................. 1510230.4

(51) Int. Cl.
*A61M 16/04* (2006.01)

(52) U.S. Cl.
CPC ........ *A61M 16/0465* (2013.01); *A61M 16/04* (2013.01); *A61M 16/0402* (2014.02); *A61M 16/0434* (2013.01)

(58) Field of Classification Search
CPC .......... A61M 16/0465; A61M 16/0402; A61M 16/04; A61M 16/0427; A61M 16/0463;
(Continued)

(56) References Cited

U.S. PATENT DOCUMENTS 3,659,612 A   5/1972  Shiley et al.
RE29,453 E * 10/1977 Weddle .................. A61F 5/445
                                                    604/344
(Continued)

FOREIGN PATENT DOCUMENTS

GB        2028139 A      3/1980

OTHER PUBLICATIONS

PCT International Search Report and Written Opinion, PCT/GB2016/000108, EPO dated Aug. 3, 2016.

*Primary Examiner* — Joseph D. Boecker
(74) *Attorney, Agent, or Firm* — Louis Woo

(57) ABSTRACT

A tracheostomy tube assembly includes an outer tube (1) and an inner cannula (2) removably inserted in the outer tube. The connector (15) on the machine end of the outer tube is rotatable through about a quarter turn and has a screw thread (30) on its inner surface. The hub (33) on the machine end of the inner cannula (2) is also formed with a screw thread (35) arranged to engage with the screw thread (30) in the connector. The inner cannula (2) is pulled into the outer tube (1), or is pushed outwardly of the tube, by rotating the connector.

10 Claims, 8 Drawing Sheets

(58) Field of Classification Search
CPC .......... A61M 16/0488; A61M 39/1011; A61M 2039/1016
See application file for complete search history.

(56) References Cited

U.S. PATENT DOCUMENTS

| | | |
|---|---|---|
| 4,304,228 A | 12/1981 | Depel |
| 4,306,743 A * | 12/1981 | Hinshaw ............... F16L 37/248 285/260 |
| 6,248,099 B1 * | 6/2001 | Bell .................. A61M 16/0465 604/264 |
| 2011/0083672 A1 * | 4/2011 | Webster ............ A61M 16/0465 128/207.15 |
| 2018/0133423 A1 * | 5/2018 | Bateman ................. A61F 5/445 604/344 |
| 2019/0290876 A1 * | 9/2019 | Fuller ............... A61M 16/0488 |

* cited by examiner

TRACHEOSTOMY TUBE ASSEMBLIES AND INNER CANNULAE

This invention relates to tracheostomy tube assemblies of the kind including an outer tracheostomy tube and an inner cannula removably inserted to extend along the bore of the tracheostomy tube.

Tracheostomy tube assemblies commonly include an outer tube and an inner tube or cannula that is a removable fit within the outer tube. The inner cannula can be removed and replaced periodically to ensure that the passage through the assembly does not become blocked by secretions. This avoids the need to remove the outer tube frequently.

The inner cannula presents various problems because it must be thin walled and a close fit within the outer tube so as to provide a large bore and thereby limit the resistance to flow of gas along the assembly. It must, however, also be sufficiently stiff to be inserted in the outer tube without buckling or kinking and must be readily removable, preferably with only minimal force being exerted on the tube. WO94/01156 and WO2004/101048 describe inner cannulae made of PTFE. EP1938857 describes an arrangement of tracheostomy tubes and inner cannulae where the hubs of the inner cannulae of different sizes are shaped differently so that they will only fit in the appropriate tracheostomy tube. EP2224985 describes an arrangement for attaching a hub to the shaft of an inner cannula. GB2056285 describes an inner cannula having a wall corrugated both externally and internally and a longitudinal groove or other reinforcement member traversing at least some of the corrugations. U.S. Pat. No. 4,817,598 describes a smooth-walled inner cannula having a ring-pull formation at its rear, machine end. U.S. Pat. No. 5,119,811 describes an inner cannula with a flared patient end and formed of two layers of different materials. U.S. Pat. No. 5,386,826 describes an inner cannula with an outer helical filament or layer of low friction material. U.S. Pat. No. 5,983,895 describes an inner cannula with straight sections at opposite ends joined by an intermediate curved section. U.S. Pat. No. 6,019,753 describes an inner cannula with two elongate regions of different flexibility so that the cannula has a plane of preferential bending. U.S. Pat. No. 6,019,753 describes an inner cannula having a shaft formed with slots to make it more flexible, the slots being covered by an outer thin sheath. U.S. Pat. No. 6,135,110 describes a curved inner cannula that is retained with the outer tube by means of a rotatable spring fitting. Tracheostomy assemblies are also available where the inner cannula is attached with a 15 mm male tapered connector that is screw threaded onto the hub of the tracheostomy tube. These arrangements have the advantage that they reduce the pulling and pushing force otherwise needed to remove and insert an inner cannula. The problem with such arrangements, however, is that, when the inner cannula is removed the tracheostomy tube lacks a connector. There is also a risk that the connector may become unscrewed from the tube inadvertently when connected in a breathing circuit and cause leakage of ventilation gas, thereby preventing effective ventilation. Other inner cannula arrangements are described in, for example, U.S. Pat. No. 6,024,730, WO2014/132015, WO2014/132016, WO2015/110773, WO2015/118288, WO2015/136232, WO2015/145099, WO2015/166200, GB2531902 and PCT/GB2016/000069.

It is an object of the present invention to provide an alternative tracheostomy tube assembly and inner cannula.

According to one aspect of the present invention there is provided a tracheostomy tube assembly of the above-specified kind, characterised in that the tracheostomy tube includes a rotatable member towards its machine end attached with a hub of the tube in a manner that allows the member to rotate relative to the hub about the axis of the hub through at least a limited angle, that the rotatable member has a surface formation on an inner surface, and that the inner cannula has a surface formation on its outer surface adapted to engage with the surface formation on the rotatable member in such a manner that rotating the rotatable member in one direction relative to the tracheostomy tube pulls the inner cannula into the tracheostomy tube and rotating in the opposite direction pushes the inner cannula out of the tracheostomy tube.

The rotatable member may be a connector of the tracheostomy tube. The connector preferably has a tapered outer surface. Alternatively, the rotatable member may a rotatable ring separate from a connector on the outer tube. The surface formations on the rotatable member and the inner cannula preferably include cooperating screw threads. The rotatable member is preferably rotatable by less than a full rotation, such as through an angle of about a quarter turn. The rotatable member and a hub of the outer tube are preferably both provided with markings that align when the rotatable member is at its locked or unlocked states. The rotatable member and a part of the outer tube may be provided with cooperating engagement members arranged to resist rotation from the locked position.

According to another aspect of the present invention there is provided an inner cannula for use in a tracheostomy assembly according to the above one aspect of the present invention.

Two embodiments of tracheostomy assemblies including an inner cannula, both in accordance with the present invention, will now be described, by way of example, with reference to the accompanying drawings, in which.

Figure 1:
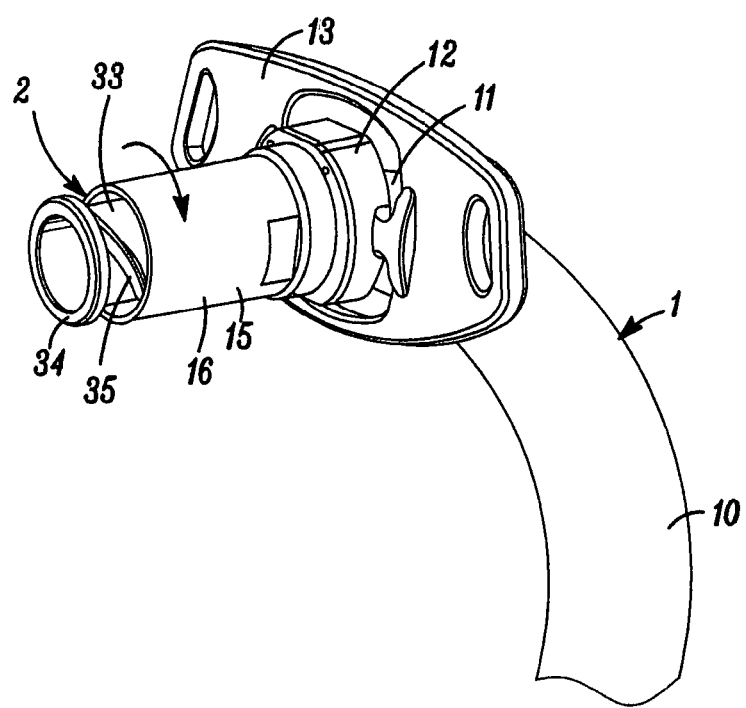
FIG. 1 is a perspective view of a first embodiment of the assembly with the inner cannula protruding from the outer tube and not fully inserted or locked in position.
Figure 5:
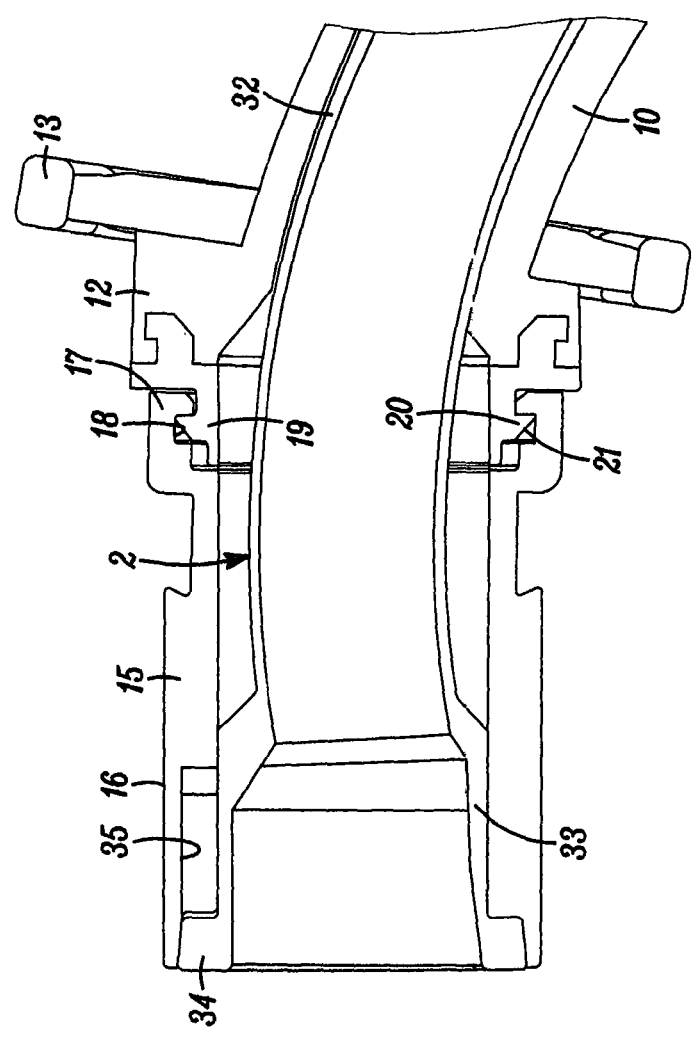
FIG. 5 is a cross-sectional side elevation view of the assembly with the inner cannula in a locked position.
Figure 6:
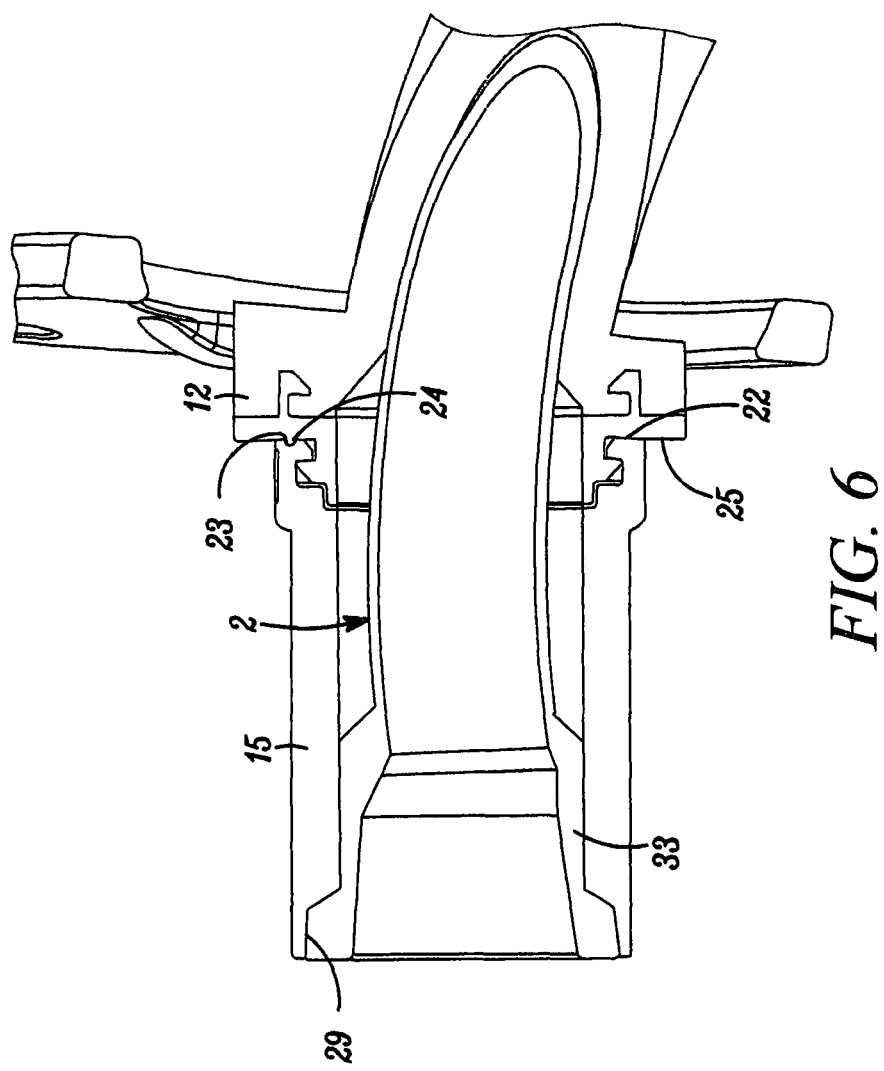
FIG. 6 is a cross-sectional view of the assembly along a plane at an angle inclined to the cross-sectional plane of FIG. 5.
Figure 7:
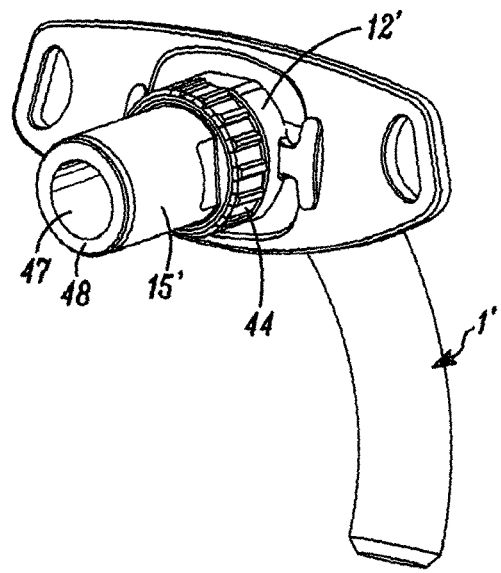
FIG. 7 is a perspective view of a second embodiment of the invention in a locked position.

With reference first to FIGS. 1 and 6, the first embodiment of the tracheostomy tube assembly comprises an outer tracheostomy tube 1 and a removable inner cannula 2 inserted within the outer tube. The outer tube 1 has a shaft 10, which is shown as being uncuffed but which could have a sealing cuff towards its patient end in the usual way. At its rear or machine end 11 the outer tube 1 has a hub 12 and flange 13 to which a retaining tape (not shown) can be fastened for securing the tube with the patient's neck. The outer tube 1 could have an internal diameter between about 2 mm and 10 mm, and its length could be between 60 mm and 200 mm. The hub 12 has a 15 mm male connector 15 secured with it, the connector having a tapered outer surface 16, which is adapted to mate with the inside surface of a cooperating female connector. The connector 15 has an inwardly-facing annular lip 17 at its forward, patient end to the rear of which extends an annular recess 18 (FIG. 5). A short collar 19 projects rearwardly from the hub 12 within the forward end of the connector 15, the collar having an outwardly-projecting lip 20 with an inclined face 21. The lip 20 on the hub 12 is aligned with the recess 18 around the connector 15 and is snapped into the recess to form a permanent attachment of the connector to the hub. The attachment provided in this way enables the connector 15 to be rotated relative to the hub 12 about the axis of the hub and through only a limited angle of about one quarter of a turn, that is, 90°.

The forward end face 22 of the connector 15 and the hub 12 have cooperating engagement members in the form of a shallow recess 23 (FIG. 6) on the connector that is adapted to receive within it a shallow projection or dimple 24 projecting rearwardly from the face 25 of the hub 12. The position of the dimple 24 and recess 23 are such that they align and engage when the connector 15 is rotated to its full extent relative to the hub 12 in the clockwise, locking direction. The size and shape of the dimple 24 and recess 23 are such that their engagement is sufficient to retain the connector 15 in the locked position against normal forces experienced during use and requires an increased initial unlocking twisting force applied by the user to release the connector so that it can be twisted anticlockwise in the unlocking direction.

Figure 2:
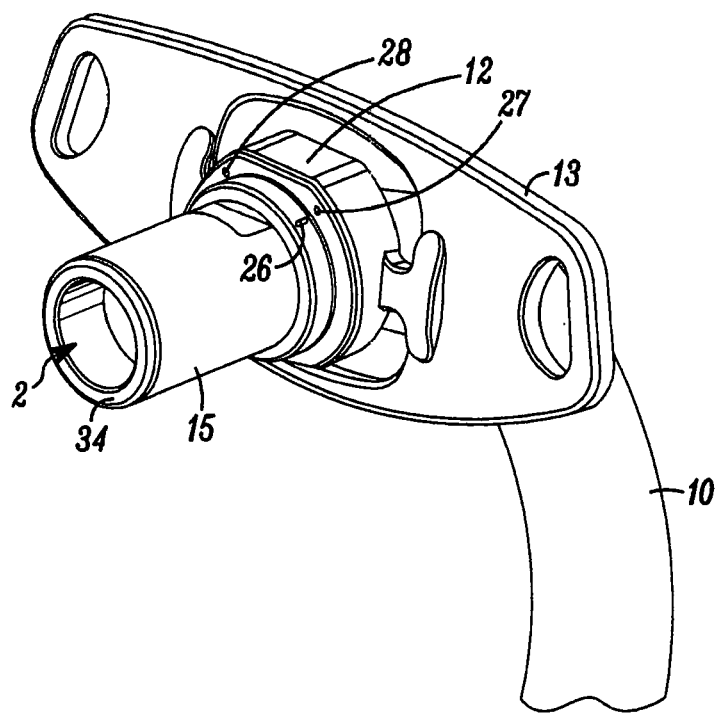
FIG. 2 is a perspective view of the assembly with the inner cannula fully inserted and locked in position.

Towards its forward, patient end the connector 15 has a visible marking 26 (FIG. 2) on its outside surface that is movable to align with one of two visible markings 27 and 28 on the rear facing face 25 of the hub 12 to indicate a locked or unlocked state respectively. It will be appreciated that the hub could just have one marking to indicate either the locked or the unlocked state.

Figure 3:
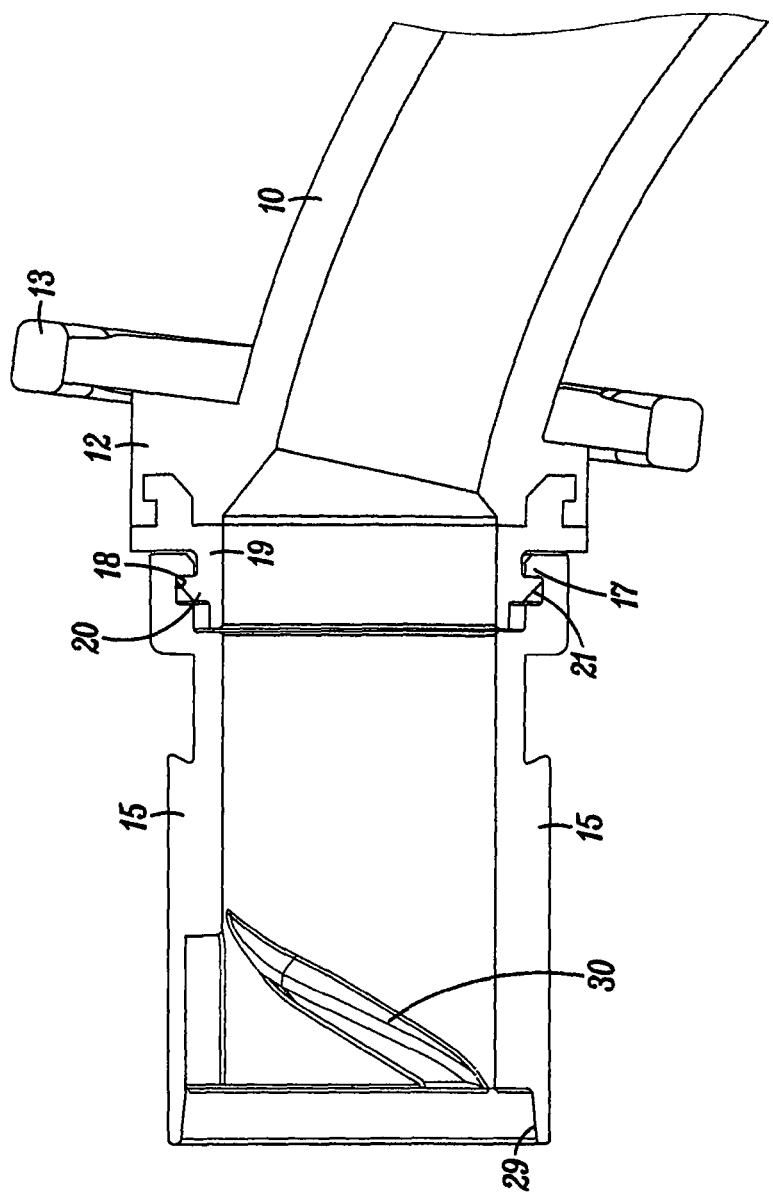
FIG. 3 is a cross-sectional side elevation of the machine end of the outer tube.

The inside of the connector 15 has an enlarged, tapered opening 29 at its open, rear or machine end (FIG. 3). Forwardly of the opening 29 the interior of the connector 15 is moulded with a surface formation 30 in the form of a screw thread with a relatively wide pitch that extends forwardly by about one third the length of the connector 15.

Figure 4:
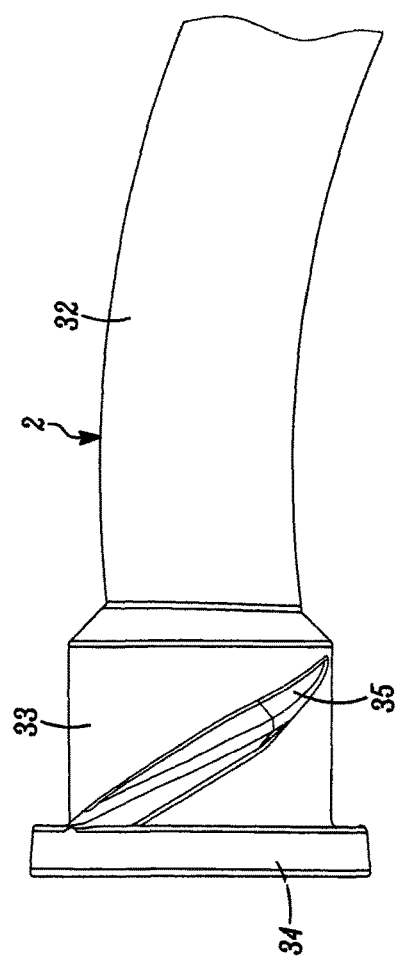
FIG. 4 is a side elevation view of the machine end of the inner cannula.

With particular reference to FIG. 4, the inner cannula 2 includes a shaft 32 of circular section and of a thin, stiff plastics material, such as PVC, polyurethane, polyethylene, polypropylene, PTFE or other flexible or semi-rigid plastics material. The external diameter of the shaft 32 is selected to be just smaller than the inner diameter of the shaft 10 of the outer tube 1 so that the inner cannula 2 can be readily inserted and removed from the outer tube. The shaft 32 is curved to the same curvature as the shaft 10 of the outer tube 1 in which it is to be used. The rear or machine end of the cannula 2 has an integral hub or machine end fitting 33 with a thicker wall than the shaft 32. The hub or machine end fitting 33 is shaped to locate and secure within the connector 15. More particularly, the hub 33 has a radially enlarged annular rim 34 at its rear, machine end that is shaped to be a snug fit within the enlarged opening 29 of the connector 15. Forwardly of the rim 34 the outer surface of the machine end fitting 33 is moulded with a surface formation in the form of a projecting screw thread 35 arranged to engage cooperatingly with the thread 30 on the inside of the connector 15. The threads 30 and 35 on the connector 15 and inner cannula 2 cooperate so that, by rotating the connector, the inner cannula can be pulled into or pushed out of the connector. The curved shape of its shaft 32 prevents the inner cannula 2 being rotated significantly when the connector 15 is rotated so that the major part of the rotational movement of the connector is translated into linear movement of the inner cannula.

FIG. 1 shows the assembly with the inner cannula 2 only partially inserted in the outer tube 1 and with a part of its rear or machine end hub 33 protruding from the connector 15. The thread 35 on the inner cannula 2 is only partially engaged with the thread 30 on the inside of the connector 15. In this state the connector 15 is in an unlocked position where it is rotated to its full extent anticlockwise. The marking 26 on the connector 15 is not visible in FIG. 1 but is aligned with the "unlocked" mark 28 on the hub 12. To load the inner cannula 2 fully in the outer tube 1 and lock it in position the user simply grips the outside of the connector 15 and twists this through a quarter turn clockwise (as indicated by the arrow in FIG. 1). In this way the threads 30 and 35 on the connector 15 and inner cannula 2 engage and act to pull the inner cannula forwardly into the outer tube until it reaches the position shown in FIG. 2 where the rear end of the inner cannula is drawn level with the rear end of the connector. In this position the marking 26 on the connector 15 has been rotated to align with the "locked" marking 27 on the hub 12.

To remove the inner cannula 2, such as when it needs to be cleaned or replaced by another cannula, the connector 15 is simply twisted back anticlockwise, which has the effect of jacking the inner cannula rearwardly to the position shown in FIG. 1 where its rim 34 can be gripped to enable it to be pulled manually fully out of the outer tube 1.

The embodiment described above has a screw thread surface on the inside of a rotatable connector that engages a screw formation on the outside of the inner cannula. However, in other embodiments the connector could be fixed and the assembly instead include some other rotatable member with an inner surface formation that engages a formation on the outside of the inner cannula.

Figure 8:
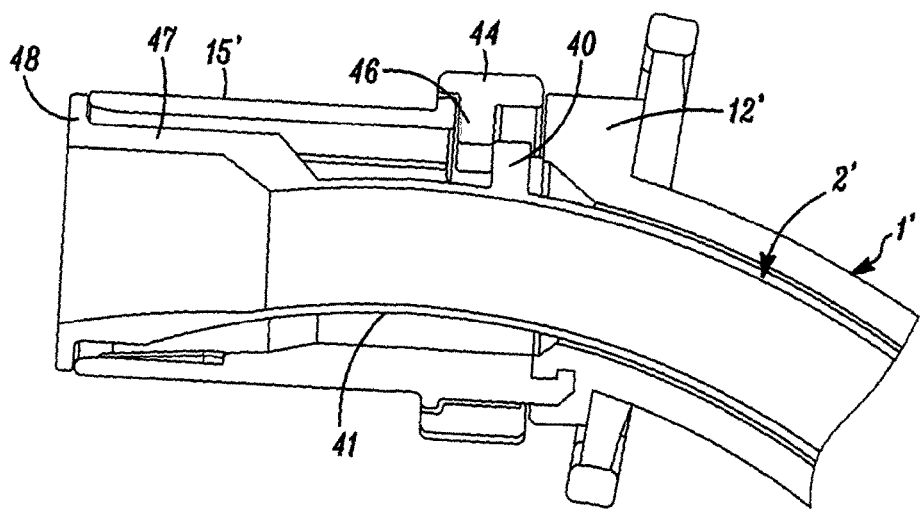
FIG. 8 is an enlarged cross-sectional side elevation view of the machine end of the second embodiment with the inner cannula locked in position.
Figure 9:
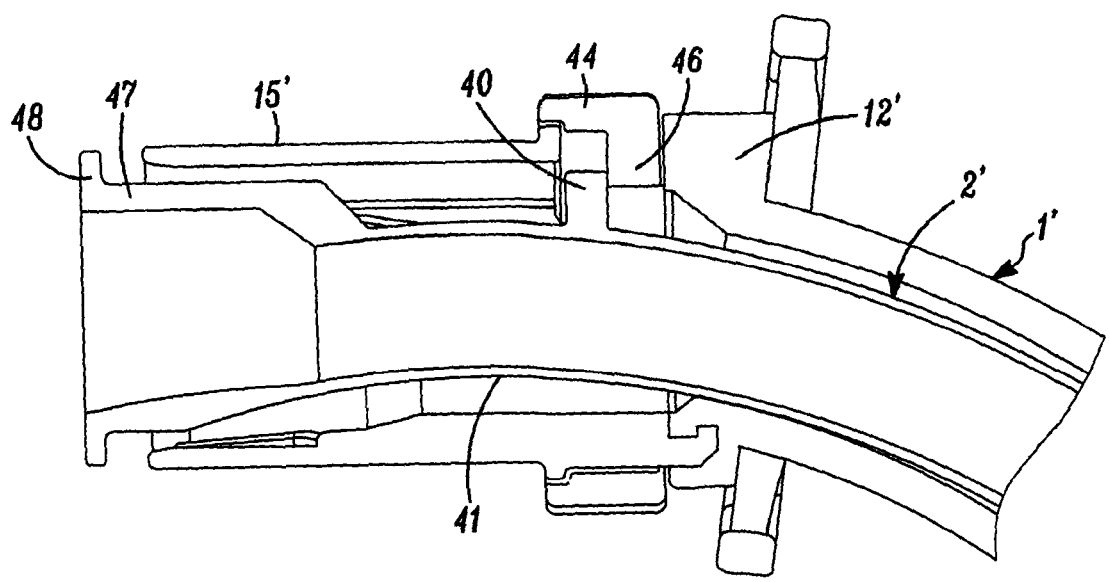
FIG. 9 is an enlarged cross-sectional side elevation view of the machine end of the second embodiment with the inner cannula partially ejected.
Figure 10:
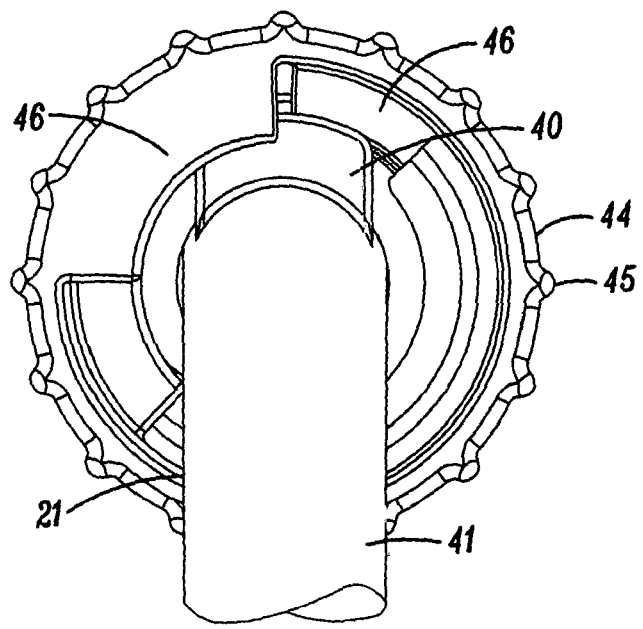
FIG. 10 is an enlarged transverse sectional view from the patient end showing the locking ring in an intermediate position.

With reference now to FIGS. 7 to 10 there is shown a second embodiment of the present invention with an inner cannula 2' that differs from the cannula described in the first embodiment in that, instead of having a screw thread formed along its hub, it has a surface formation in the form of a narrow lug 40 projecting outwardly from the shaft 41 upwardly, that is, on the outside of the curvature of the shaft. The outer, tracheostomy tube 1' also differs in having a fixed connector 15' and a rotatable locking ring 44 mounted coaxially of the connector, between the connector and the hub 12'. The outer edge 45 of the ring 44 is knurled to improve grip. The mounting of the locking ring 44 on the hub 12' allows for only limited angular rotation of 90°. The inner surface of the locking ring 44 has a short, divided screw thread 46 shaped to engage opposite faces of the lug 40 on the inner cannula 2'. FIG. 8 shows a condition where the locking ring 44 is rotated fully clockwise and it can be seen that one part of the thread 46 on the ring lies on the outer, left-hand surface of the lug 40, thereby forcing the inner cannula 2' inwardly into the outer tube 1' until the rim 48 at the end of the inner cannula hub 47 engages the outer end of the connector 15'. Rotating the locking ring 44 in the opposite, anticlockwise sense brings the rearwardly-facing surface of the other part of the screw thread 46 on the ring into engagement with the forwardly-facing surface of the lug 40 on the inner cannula 2', thereby pushing the inner cannula out of the outer tube 1' by a short distance, as shown in FIG. 9. The distance by which the locking ring 44 ejects the inner cannula 2' is only small but is sufficient to enable the rim 48 at the end of the inner cannula to be gripped so that it can be pulled fully out of the outer tube by hand.

The arrangement of the present invention can be used to overcome the problems of previous arrangements where the action of removing and replacing an inner cannula results in uncomfortable and possibly damaging forces applied to the delicate tissues around the patient's stoma. The twist mechanism of the present invention ensures that the inner cannula is drawn smoothly into or pushed smoothly out of the outer tube. The invention also allows for the connector to remain securely attached with the outer tube so that it can be used with or without an inner cannula.

The invention claimed is:

1. A tracheostomy tube assembly including an outer tracheostomy tube having a bore and a machine end and an inner cannula having a rear end removably inserted to extend along the bore of the tracheostomy tube, characterised in that the tracheostomy tube includes a male tapered connector towards its machine end rotatably attached with a hub of the outer tracheostomy tube in a manner that allows the connector to rotate relative to the hub about an axis of the hub through at least a limited angle, that the rotatable connector has a rear end and has a screw thread on an inner surface, and that the inner cannula has a screw thread on its outer surface adapted to engage with the screw thread on the rotatable connector in such a manner that rotating the connector in one direction relative to the tracheostomy tube pulls the inner cannula fully into the tracheostomy tube so that the rear end of the inner cannula is drawn level with the rear end of the connector and rotating the connector relative to the tracheostomy tube in a direction opposite to the one direction pushes at least the rear end of the inner cannula out of the rear end of the connector if the inner cannula was previously fully loaded into the tracheostomy tube.

2. A tracheostomy tube assembly according to claim 1, characterised in that the connector is rotatable by less than a full rotation.

3. A tracheostomy tube assembly according to claim 2, characterised in that the connector is rotatable through an angle of about a quarter turn.

4. A tracheostomy tube assembly according to claim 1, characterised in that the connector and the hub of the outer tube are both provided with markings that align when the connector is at its locked or unlocked states.

5. A tracheostomy tube assembly according to claim 1, characterised in that the connector and a part of the outer tube are provided with cooperating engagement members arranged to resist rotation from a locked position of the connector.

6. A tracheostomy tube assembly according to claim 1, wherein the rear end of the inner cannula comprises an annular rim and the rear end of the connector comprises an enlarged opening configured to receive the annular rim.

7. In combination,
an inner cannula having a shaft, a rear end and a fitting having formed on its outer surface a screw thread;
an outer tracheostomy tube having a bore and a hub;
a connector having a rear end and an opening defined by an inner surface rotatably secured to the hub of the outer tracheostomy tube, the connector rotatable relative to the hub about an axis of the hub through at least a limited angle, a screw thread formed on the inner surface of the connector;
wherein the inner cannula is adapted to be removably inserted to extend along the bore of the tracheostomy tube; and
wherein the screw thread on the outer surface of the inner cannula and the screw thread on the inner surface of the connector are adapted to engage with each other such that rotating the connector in one direction relative to the tracheostomy tube pulls the inner cannula fully into the tracheostomy tube with the rear end of the inner cannula being drawn level with the rear end of the connector and rotating the connector in an opposite direction to the one direction relative to the tracheostomy tube pushes at least the rear end of the inner cannula out of the rear end of the connector if the inner cannula was previously fully loaded into the tracheostomy tube.

8. The combination of claim 7, wherein the hub of the outer tracheostomy tube has an outwardly projecting collar that snap fits to a recess at a distal end of the connector so that a permanent attachment that enables the connector to rotate relative to the hub is formed between the hub and the connector.

9. The combination of claim 7, wherein the connector and the hub of the outer tracheostomy tube are both provided with markings that align when the connector is at its locked or unlocked states.

10. The combination of claim 7, wherein the opening at the rear end of the connector has an enlarged tapered opening adapted to receive an enlarged annular rim at the rear end of the inner cannula when the connector is rotated in the one direction to pull the inner cannula into the tracheostomy tube.

* * * * *